(12) United States Patent
Alvarez

(10) Patent No.: US 6,773,411 B1
(45) Date of Patent: Aug. 10, 2004

(54) KNEE BRACE

(75) Inventor: Lazaro Alvarez, Miami, FL (US)

(73) Assignee: Innovations Beyond Limitations, Inc., Miami, FL (US)

( * ) Notice: Subject to any disclaimer, the term of this patent is extended or adjusted under 35 U.S.C. 154(b) by 0 days.

(21) Appl. No.: 10/424,898

(22) Filed: Apr. 29, 2003

(51) Int. Cl.[7] ................................................ A61F 5/00
(52) U.S. Cl. .............................. 602/27; 602/62; 602/63
(58) Field of Search .......................... 602/23, 26, 27, 602/60–65; 128/882

(56) References Cited

U.S. PATENT DOCUMENTS

| | | | | |
|---|---|---|---|---|
| 3,804,084 A | * | 4/1974 | Lehman | |
| 4,366,813 A | * | 1/1983 | Nelson | 2/24 |
| 4,445,505 A | | 5/1984 | Labour et al. | 128/80 |
| 5,016,621 A | * | 5/1991 | Bender | 128/80 C |
| 5,139,477 A | | 8/1992 | Peters | 602/26 |
| 5,656,023 A | * | 8/1997 | Caprio, Jr. et al. | 602/63 |
| 5,865,777 A | * | 2/1999 | Detty | 602/26 |

* cited by examiner

*Primary Examiner*—Michael A. Brown
(74) *Attorney, Agent, or Firm*—Albert Boroas; Jesus Sanchelima

(57) ABSTRACT

A flexible knee brace that provides support to the knee, meniscus, ligaments, and muscles of the leg, and assists with the rehabilitation of the knee when injured, pre-surgery, and post-surgery. The knee brace is made of an elasticized sleeve worn over the leg and spanning the knee. The sleeve has a plurality of channels running vertically on each side of the patella, nearly the full length of the sleeve. The channels house flexible elongated strips that may be removed or added to adjust the bending resistance of the knee brace. The knee brace is secured in place by an elastic strap sewn onto the sleeve and running laterally above the patella.

5 Claims, 4 Drawing Sheets

KNEE BRACE

BACKGROUND OF THE INVENTION

1. Field of the Invention

The present invention relates to knee braces, and more particularly, to a knee brace that provides support to the knee, meniscus, ligaments, and muscles of the leg, and assists with the rehabilitation of the knee when injured, pre-surgery, and post-surgery.

2. Description of the Related Art

Many designs for knee braces have been designed in the past. None of them, however, includes a plurality of elongated channels running vertically on each side of the patella, nearly the full length of the knee brace sleeve. The channels house flexible elongated strips that may be removed or added, enabling the patient to control the amount of bending resistance the knee brace has.

Applicant believes that the closest reference corresponds to U.S. Pat. No. 5,139,477 issued to Peters for Knee Sleeve. However, it differs from the present invention because Peters teaches a ready-to-wear pull-on knee support adapted to be placed over the knee. The support comprising a generally cylindrical body comprising a resilient flexible unitary sleeve, which is preferably formed from an elasticized fabric laminate. The elasticized fabric laminate includes an open-cell polymeric foam core, an outer surface comprising an elasticized fabric having a looped structure and an inner surface for wear next to the body, comprising an elasticized cotton fabric. The support includes integral parallel proximal and distal encircling straps adapted to encircle the lower thigh and upper calf, respectively, medial and lateral stabilizing or reinforcing straps and infinitely adjustable proximal and distal posterior closure means. A patella opening can be provided for patella support. A popliteal opening can be provided or the popliteal area may be covered, in which case the popliteal area is formed with a C-seam extending outwardly from the distal and proximal closure means over the outer popliteal area.

Applicant believes that another reference corresponds to U.S. Pat. No. 4,445,505 issued to Labour et al. for Knee Brace For Preventing Lateral Displacement Of The Patella. However, it differs from the present invention because Labour et al. teaches a knee brace for preventing lateral displacement of the patella, made of an elasticized sleeve worn over the leg and spanning the knee. The sleeve carries a pair of pads, one of, which lies immediately adjacent the outer edge of the patella and blocks the patella from lateral displacement. The second pad overlies the medial femoral epicondyl to prevent the sleeve from rotating outwardly as forces are applied against the first pad by the patella. The pads are locked in place by an elastic strap secured to the sleeve and running laterally to medially over the knee.

Other patents describing the closest subject matter provide for a number of more or less complicated features that fail to solve the problem in an efficient and economical way. None of these patents suggest the novel features of the present invention.

SUMMARY OF THE INVENTION

A knee brace for rehabilitating an injured knee, comprising a tubular sleeve assembly made of an elastic webbing material. The sleeve assembly is designed to fit over a leg and extend from below the knee upwardly to the thigh of the leg. In addition, an elongated pocket assembly is attached to the sleeve assembly. The elongated pocket assembly is positioned on the sleeve assembly longitudinally over the patella of the knee when the sleeve assembly is worn on the leg. The elongated pocket assembly has at least one vertical channel. The at least one vertical channel selectively houses at least one elongated strip having a predetermined bending resistance so as to impede bending of the leg at the knee.

The elongated strip is removable, enabling a patient to remove and insert additional elongated strips of various gauges to adjust the predetermined bending resistance of the knee brace. As the predetermined bending resistance of the knee brace increases, support to the knee, meniscus, ligaments, and muscles of the leg increases, resulting in lesser stress to the knee. As the predetermined bending resistance to the knee brace decreases, support to the knee, meniscus, ligaments, and muscles of the leg decreases, resulting in greater stress to the knee.

The instant invention further comprises a strap assembly secured to the sleeve assembly adjacent to the elongated pocket assembly that extends around the leg. Fastening means secured thereon fastening the strap assembly to the sleeve assembly.

The channel extends substantially longitudinally the full length of the sleeve assembly on either side of the patella. The sleeve assembly is stretchable both in a circumferential and axial direction. The strap assembly is stretchable lengthwise and the fastening means is a hook and loop fastener. The strap assembly when tightens above the patella.

A method of rehabilitating an injured knee with a knee brace, comprises:

A) diagnosing the severity of injury to a knee;

B) weighing and determining the athletic ability of a patient in need of knee rehabilitation;

C) inserting a predetermined number of elongated strips into each channel of said knee brace;

D) slipping said knee brace onto said knee; and

E) adding or removing said elongated strips to adjust the pressure on said knee, meniscus, ligaments, and muscles of a leg of said patient until said knee is rehabilitated.

It is therefore one of the main objects of the present invention to provide a knee brace having channels that house removable flexible elongated strips, enabling a patient to control the amount of bending resistance the knee brace has.

It is another object of this invention to provide a knee brace that is comfortable and provides support to the knee, meniscus, ligaments, and muscles of the leg, and assists with the rehabilitation of the knee when injured, pre-surgery, and post-surgery.

It is another object of this invention to provide a knee brace that assists patients with arthritic conditions.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
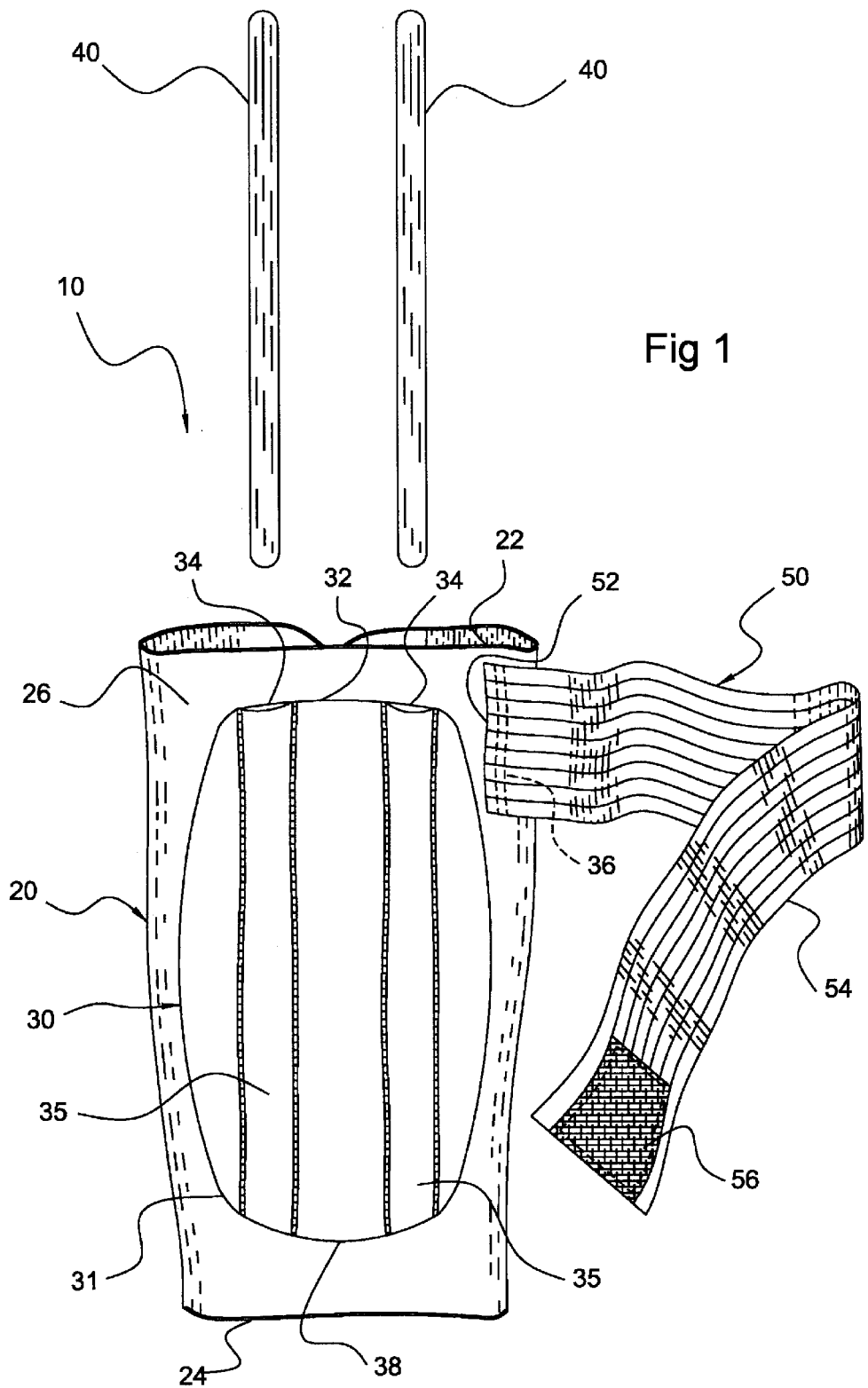
FIG. 1 represents an isometric view of the instant invention with its flexible elongated strips.

Referring now to the drawings, where the present invention is generally referred to with numeral 10, it can be observed that it basically includes sleeve assembly 20, pocket assembly 30, and strap assembly 50.

As seen in FIG. 1, the instant invention comprises elasticized sleeve assembly 20, which is slid onto the leg and worn over the knee. Sleeve assembly 20 has ends 22 and 24, and extends from the upper portion of the calf of the leg, end 24, to the thigh, end 22. The brace shown in the illustrations is designed to fit over either leg.

Sleeve assembly 20 is stretchable both in a longitudinal and circumferential direction and preferably is knitted of a soft cotton yarn and elasticized thread so as to be comfortable on the body. In addition, the material selected for sleeve assembly 20 should be lightweight and be sufficiently yielding so as to conform to the contours of the leg when worn. The sleeve assembly 20 in an adult size may be approximately ten inches long and twelve inches in circumference at the middle. Of course the size may vary depending upon the body build of the patient to wear the device.

As seen in the illustrated embodiment, pocket assembly 30 is knitted onto sleeve assembly 20. In the preferred embodiment, stitching 36 defines two channels 35, one on each side of the patella. In an alternate embodiment, more than one channel 35 may be defined on each side of the patella. Pocket assembly 30 has ends 32 and 38. Also seen are elongated strips 40, which slide into channels 35 through their respective slits 34 at end 32.

Figure 2:
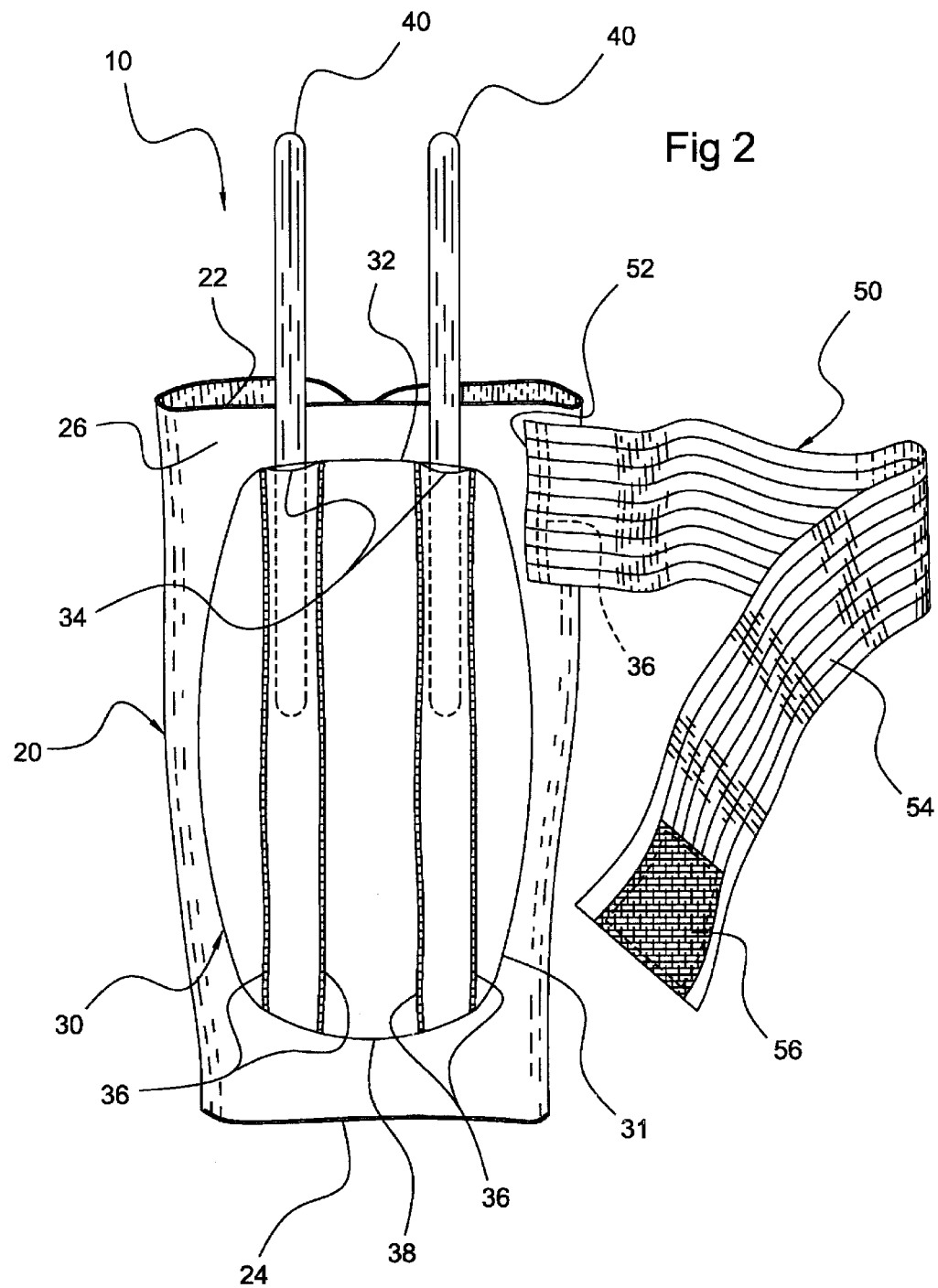
FIG. 2 shows an isometric view of the instant invention with its flexible elongated strips partially inserted in their respective channels.

As seen in FIG. 2, each elongated strip 40 is partially inserted within its respective channel 35. Pocket assembly 30 is sewn onto sleeve assembly 20 with stitching 31. Once inserted, elongated strips 40 stay within their respective channel 35 and do not cross or overlap one another. Elongated strips 40 extend substantially the full length of sleeve assembly 20 and typically may be made of a spring-like material such as flat coil wire affording considerable flexibility to the brace. The principal purpose of elongated strips 40 is to impede bending of the leg at the knee with predetermined resistances. The predetermined resistances being the gauge and/or material of elongated strips 40.

In the preferred embodiment, front portion 26 of sleeve assembly 20 does not include an opening for the patella. However, in an alternate embodiment, an opening to accommodate the patella of the patient may be presented for patient comfort. The opening is aligned with the patella when sleeve assembly 20 is worn. The opening may relieve pressure against the patella, prevents abrasion of the skin during vigorous activity of the patient, and increases the flexibility of the instant invention 10 at the patella. Similarly, in the preferred embodiment, rear portion 28, seen in FIG. 3, of sleeve assembly 20 does not include an opening for the popliteal area. However, in an alternate embodiment, an opening to accommodate the popliteal area of the patient may be presented for patient comfort. The opening is aligned with the popliteal area when sleeve assembly 20 is worn. The opening may relieve pressure against the popliteal area, prevents abrasion of the skin during vigorous activity of the patient, and increases the flexibility of the instant invention 10 at the popliteal area.

Figure 3:
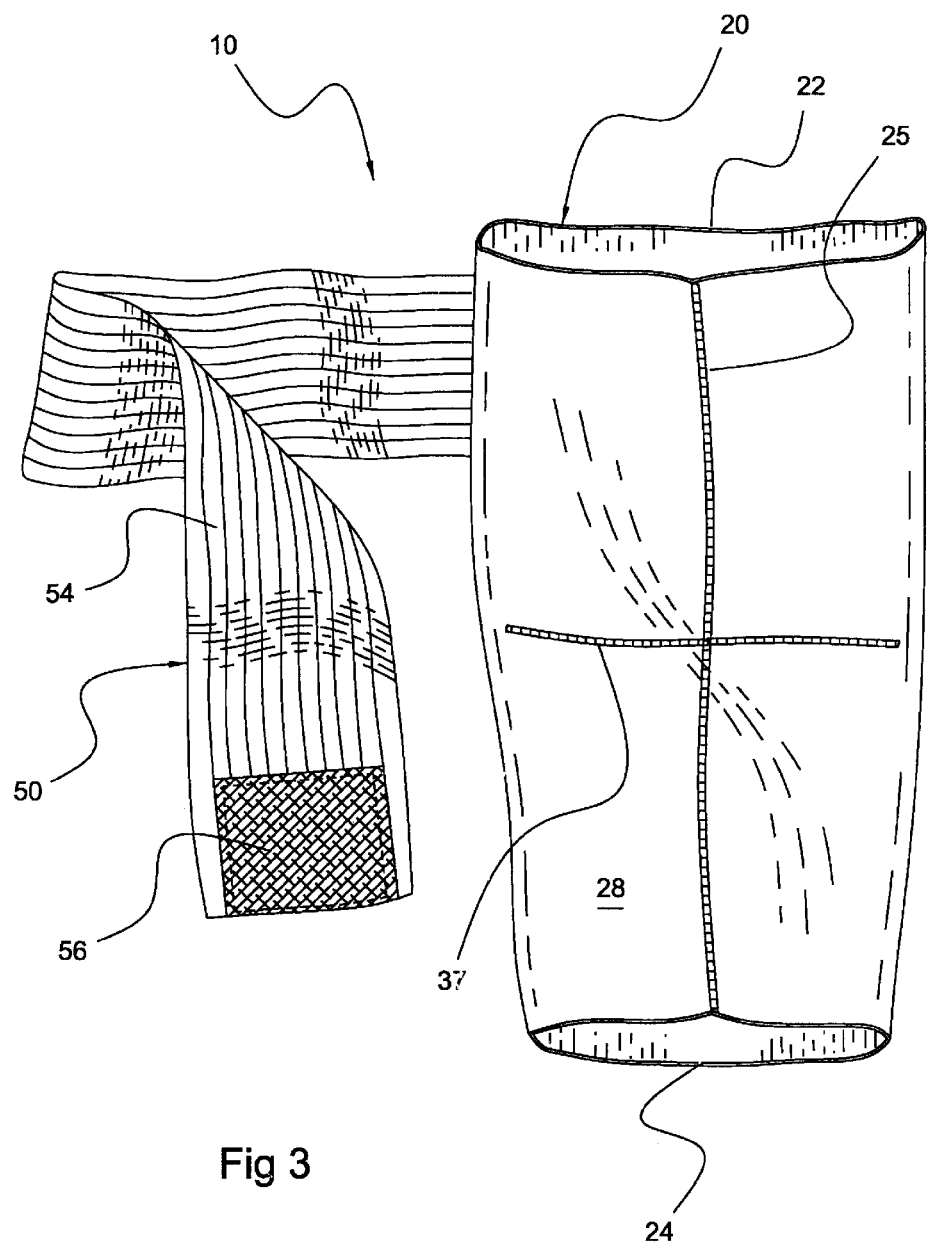
FIG. 3 shows an isometric rear view of the instant invention.

As seen in FIGS. 1–3, strap assembly 50 is made of elastic webbing stretchable lengthwise but non-stretchable across its width in the preferred embodiment. Lateral end 52 is secured with stitching 36 to the outer surface of sleeve assembly 20, just above the patella area of the patient. When securing the knee brace, strap assembly 50 extends laterally around front portion 26, wrapping around rear portion 28 and continues around the leg of the patient the full length of strap assembly 50. Free end 54 has a Velcro-type fastener 56 stitched thereon and is designed to releasably lock onto the female type strap assembly 50 when wrapped around the leg of the patient. It will be appreciated that the patient may pull strap assembly 50 as tightly as desired to effectively apply pressure above the patella.

Figure 5:
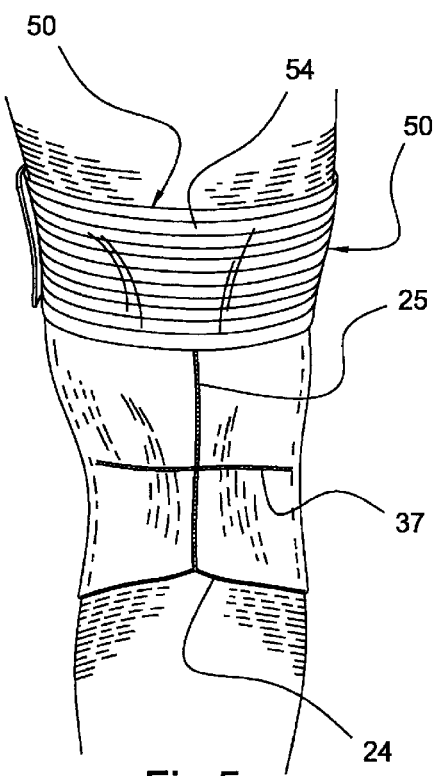
FIG. 5 illustrates a perspective rear view of the instant invention worn by the patient.

As seen in FIGS. 3 and 5, sleeve assembly 20 has stitching 37 and 25. In the preferred embodiment, stitching 37 is placed behind the patella to allow the patient to easily bend at the knee. Stitching 25 is defined simply for manufacturing purposes in the illustrated embodiment.

Figure 4:
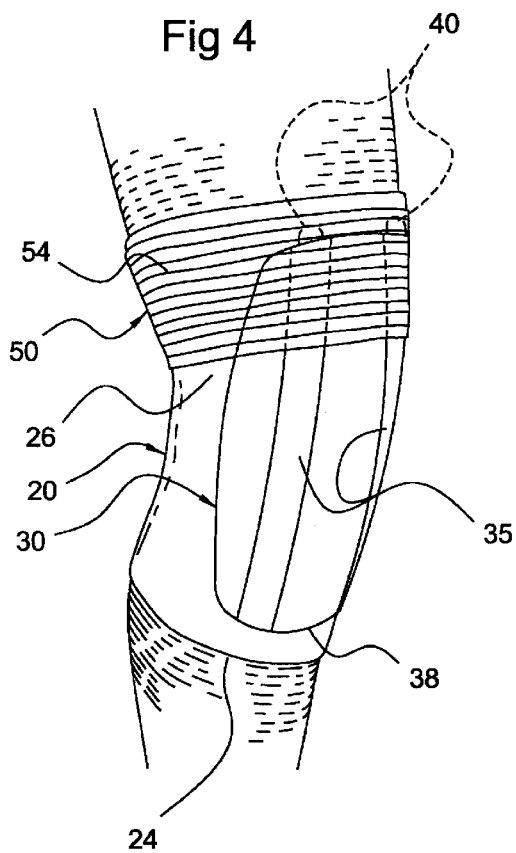
FIG. 4 illustrates a perspective view of the instant invention worn by the patient when their leg is straight.
Figure 6:
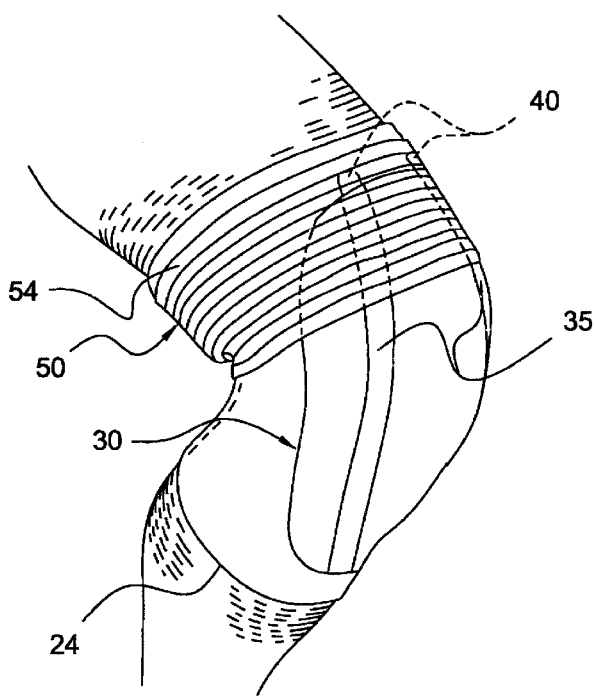
FIG. 6 illustrates a perspective view of the instant invention worn by the patient when their leg is bent.

It is noted that when properly worn, the patient will feel the knee brace spring back to its natural position, seen in FIG. 4, from the bent position, seen in FIG. 6, thus supporting the knee, meniscus, ligaments, and muscles of the leg.

In summary, the knee brace of this invention, unlike the prior art devices in combination, enables a patient to impede bending of the leg at the knee with predetermined resistances. The patient has the ability to remove or insert additional elongated strips 40, of various gauges, to adjust the bending resistance of the knee brace.

As the bending resistance of the knee brace increases, the support to the knee, meniscus, ligaments, and muscles of the leg increases. Thus, resulting in lesser stress to the knee. As the bending resistance to the knee brace decreases, the support to the knee, meniscus, ligaments, and muscles of the leg decreases. Thus, resulting in greater stress to the knee.

In the preferred embodiment, the patient may insert one or two elongated strips in each channel 35. The elongated strips may be made of metal, plastic, or any other material that is flexible, yet retains its natural position.

The present invention also includes a method of rehabilitating an injured knee with a knee brace, comprising:

A) diagnosing the severity of injury to said knee;

B) weighing and determining the athletic ability of a patient in need of knee rehabilitation;

C) inserting a predetermined number of elongated strips into each channel of said knee brace;

D) slipping said knee brace onto said knee; and

E) adding or removing said elongated strips to adjust the pressure on said knee, meniscus, ligaments, and muscles of a leg of said patient until said knee is rehabilitated.

Step A) of the method includes, diagnosing the severity of injury to the patient's knee. This step is to be performed by a trained medical professional and an orthopedic doctor whenever possible. Proper diagnosis will help establish the amount of bending resistance the knee brace should have. Keeping in mind that as the bending resistance to the knee brace increases, the support to the knee, meniscus, ligaments, and muscles of the leg increases. Thus, resulting in lesser stress to the knee. As the bending resistance to the knee brace decreases, the support to the knee, meniscus, ligaments, and muscles of the leg decreases. Thus, resulting in greater stress to the knee.

Step B) of the method includes, weighing and determining the athletic ability of a patient in need of knee rehabilitation. Proper determination will help establish the amount of bending resistance the knee brace should have according to the patient's weight.

Step C) of the method includes, inserting a predetermined number of elongated strips into each channel of the knee brace. The predetermined number of elongated strips is established with the results of Steps A)–C) above. Each elongated strip is slid into its respective channel through its respective slit.

Step D) of the method includes slipping the knee brace onto the injured knee.

Step E) of the method includes, adding or removing the elongated strips to adjust the pressure on the knee, meniscus, ligaments, and muscles of a leg of the patient, until the injured knee is rehabilitated.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A knee brace for rehabilitating an injured knee, comprising:

A) a tubular sleeve assembly made of an elastic webbing material, said sleeve assembly being designed to fit over a leg and extend from below the knee upwardly to the thigh of said leg, said tubular sleeve assembly also having first and second stitching, said first stitching being horizontal behind said knee to facilitate bending of said knee and said second stitching being vertical behind said knee to facilitate manufacturing of said tubular sleeve assembly;

B) an elongated pocket assembly attached to said sleeve assembly, said elongated pocket assembly being positioned on said sleeve assembly longitudinally over the patella of said knee when said sleeve assembly is worn on said leg, said elongated pocket assembly having at least one vertical channel, said at least one vertical channel selectively housing at least one elongated strip having a predetermined bending resistance so as to impede bending of said leg at said knee, said elongated strip is removable, enabling a patient to remove and insert additional said elongated strips of various gauges to adjust said predetermined bending resistance of said knee brace, said predetermined bending resistance of said knee brace increases, support to knee, meniscus, ligaments, and muscles of said leg increases, resulting in lesser stress to the knee and as said predetermined bending resistance to said knee brace decreases, said support to said knee, said meniscus, said ligaments, and said muscles of said leg decreases, resulting in greater stress to said knee; and C) a strap assembly secured to said sleeve assembly adjacent to said elongated pocket assembly and extending around said leg, and having fastening means secured thereon for fastening said strap assembly to said sleeve assembly, said strap assembly when tightened extending above said patella for placement ease and comfort.

2. The knee brace set forth in claim 1, further characterized in that said channel extends substantially longitudinally the full length of said sleeve assembly on either side of said patella.

3. The knee brace set forth in claim 2, further characterized in that said sleeve assembly is stretchable both in a circumferential and axial direction.

4. The knee brace set forth in claim 3, further characterized in that said strap assembly is stretchable lengthwise and said fastening means is a hook and loop fastener.

5. A knee brace for rehabilitating an injured knee, comprising:

A) a tubular sleeve assembly made of an elastic webbing material, said sleeve assembly being designed to fit over a leg and extend from below the knee upwardly to the thigh of said leg, said tubular sleeve assembly also having first and second stitching, said first stitching being horizontal behind said knee to facilitate bending of said knee and said second stitching being vertical behind said knee to facilitate manufacturing of said tubular sleeve assembly, said tubular sleeve assembly is stretchable both in a circumferential and axial direction;

B) an elongated pocket assembly attached to said sleeve assembly, said elongated pocket assembly being positioned on said sleeve assembly longitudinally over the patella of said knee when said sleeve assembly is worn on said leg, said elongated pocket assembly having at least one vertical channel, said at least one vertical channel selectively housing at least one elongated strip having a predetermined bending resistance so as to impede bending of said leg at said knee, said elongated strip is removable, enabling a patient to remove and insert additional said elongated strips of various gauges to adjust said predetermined bending resistance of said knee brace, said predetermined bending resistance of said knee brace increases, support to knee, meniscus, ligaments, and muscles of said leg increases, resulting in lesser stress to the knee and as said predetermined bending resistance to said knee brace decreases, said support to said knee, said meniscus, said ligaments, and said muscles of said leg decreases, resulting in greater stress to said knee, said channel extends substantially longitudinally the full length of said sleeve assembly on either side of said patella; and C) a strap assembly secured to said sleeve assembly adjacent to said elongated pocket assembly and extending around said leg, and having fastening means secured thereon for fastening said strap assembly to said sleeve assembly, said strap assembly when tightened extending above said patella for placement ease and comfort, said strap assembly is stretchable lengthwise and said fastening means is a hook and loop fastener.

* * * * *